United States Patent
Joshi et al.

(10) Patent No.: US 6,931,092 B2
(45) Date of Patent: Aug. 16, 2005

(54) SYSTEM AND METHOD FOR THERMAL MANAGEMENT OF CT DETECTOR CIRCUITRY

(75) Inventors: Ashutosh Joshi, Bangalore (IN); William Edward Burdick, Jr., Schenectady, NY (US); Sandeep Shrikant Tonapi, Niskayuna, NY (US); Joseph Lacey, Cambridge, WI (US)

(73) Assignee: General Electric Company, Niskayuna, NY (US)

( * ) Notice: Subject to any disclaimer, the term of this patent is extended or adjusted under 35 U.S.C. 154(b) by 8 days.

(21) Appl. No.: 10/609,755

(22) Filed: Jun. 30, 2003

(65) Prior Publication Data

US 2004/0264631 A1 Dec. 30, 2004

(51) Int. Cl.⁷ .............................................. G01N 23/083
(52) U.S. Cl. .................................... 378/19; 250/370.15
(58) Field of Search ...................... 250/370.09, 370.15; 378/19, 98.8; 257/713, 714, 722

(56) References Cited

U.S. PATENT DOCUMENTS

| | | | | |
|---|---|---|---|---|
| 4,831,639 A | * | 5/1989 | Harke | 378/19 |
| 5,216,250 A | * | 6/1993 | Pellegrino et al. | 250/370.09 |
| 5,235,191 A | * | 8/1993 | Miller | 250/486.1 |
| 5,444,752 A | * | 8/1995 | Dobbs et al. | 378/19 |
| 5,596,228 A | * | 1/1997 | Anderton et al. | 257/714 |
| 5,857,007 A | | 1/1999 | Haq et al. | 378/19 |
| 6,005,911 A | * | 12/1999 | Cheung | 378/37 |
| 6,249,563 B1 | * | 6/2001 | Snyder et al. | 378/19 |
| 6,495,836 B1 | * | 12/2002 | Hata | 250/370.09 |
| 6,621,084 B1 | * | 9/2003 | Wainer et al. | 250/370.09 |
| 6,658,082 B2 | * | 12/2003 | Okumura et al. | 378/19 |
| 2002/0054659 A1 | | 5/2002 | Okumara et al. | 378/19 |

FOREIGN PATENT DOCUMENTS

JP  06061385 A  *  3/1994  .......... H01L/23/36

* cited by examiner

*Primary Examiner*—Craig E. Church
*Assistant Examiner*—Thomas R. Artman
(74) *Attorney, Agent, or Firm*—Fletcher Yoder

(57) ABSTRACT

A computed tomography (CT) system comprises an X-ray radiation source to project a plurality of X-ray beams through an object and a detector array comprising a plurality of detector assemblies. Each of the detector assembly further comprises a detector subassembly adapted to detect the X-ray beams and further adapted to convert the X-ray beams to a plurality of electrical signals and at least one integrated circuit array, for example, data acquisition chip array to acquire data corresponding to the electrical signals. The integrated circuit array, for example, data acquisition chip array further comprises a plurality of integrated circuits, such as, data acquisition chips mounted on at least one printed circuit board and a thermal management system adapted for thermal communication between the data acquisition chip array and a heat sink assembly to control thermal environment of each detector assembly. The heat sink further comprises a spreader plate extending over 2 or more data acquisition chips to reduce the temperature difference within the data acquisition chips.

40 Claims, 14 Drawing Sheets

SYSTEM AND METHOD FOR THERMAL MANAGEMENT OF CT DETECTOR CIRCUITRY

BACKGROUND OF THE INVENTION

The present invention relates generally to the field of computed tomography scanning systems and more particularly to thermal management of circuits used in such computed tomography systems.

Generally, a computed tomography (CT) scanning system for acquiring and processing image data of an object of interest, for example a human patient, includes a source of X-ray radiation, typically an X-ray tube. Operationally, the X-ray radiation source projects the X-ray beam towards the object being imaged and further towards a detector array made up of a plurality of detector assemblies. The detector assemblies detect the X-ray radiation after passing through or around the object, and subsequently convert this X-ray radiation to a plurality of electrical signals that represent the intensity of the incident X-ray radiation. These electrical signals are acquired and processed further to construct an image of the features within the object. A rotational system, typically including a gantry fixedly attached to the X-ray source and the detector array, enables them to rotate at least one full 360° turn around the object.

Operationally, as the X-ray radiation source and the detector array fixedly attached to the gantry rotate, an integrated circuit array, such as a data acquisition system (DAS) circuit or chip array, having a plurality of integrated circuits, such as, data acquisition chips mounted on the printed circuit board of the detector assembly, collect data corresponding to electrical signals representing attenuation of the X-ray radiation after passing through or around the object. During operation, thermal energy is generated by the data acquisition chips as they are powered to complete their processing functions. A particular challenge in such systems, then, arises from the need to remove this energy from the chips and, to the extent possible, to maintain the chips in a relatively isothermal condition (i.e. reduce the temperature variation between separate chips or processing circuits).

Generally, in conventional approaches the thermal load generated from the data acquisition chip array of a conventional CT scanning system is mitigated through an air circulating system that blows air over the data acquisition chips. This method of cooling may not have the capability to maintain the data acquisition chips in an isothermal condition and significant variation in temperature may be observed between the data acquisition chips. Variation of temperature in the data acquisition chips is also observed during the transient phases when the CT system is rotating or in a stationary position. Moreover, in improved CT scanning systems the width of the detector assembly building the detector array is larger and more densely populated as compared to conventional CT scanning systems in order to accommodate wider array of axial coverage of the patient. Therefore, the thermal load generated from the data acquisition chip array of the detector assembly of such improved CT scanning systems is relatively higher than the heat load generated from conventional CT systems.

There is a need, therefore, for a thermal management system suitable to handle this additional heat load and to reduce the variation in the temperature of the data acquisition chips of the detector assembly of a CT system is desirable.

BRIEF DESCRIPTION OF THE INVENTION

The present invention provides a thermal management approach designed to respond to such needs. Briefly, in accordance with some aspects of the present technique, a computed tomography (CT) system comprises an X-ray radiation source to project a plurality of X-ray beams through an object. A detector array comprises a plurality of detector assemblies. Each detector assembly further comprises a detector subassembly adapted to detect the X-ray beams, and further adapted to convert the X-ray beams to a plurality of electrical signals. At least one circuit board assembly is coupled to the detector subassembly to acquire data corresponding to the electrical signals. The circuit board assembly comprises a plurality of integrated circuits, such as data acquisition chips mounted on at least one printed circuit board. A thermal management system is adapted for thermal communication between the integrated circuits, such as the data acquisition chips and a heat sink assembly to control the thermal environment of each detector assembly. The heat sink assembly further comprises a spreader plate extending over two or more integrated circuits, such as, data acquisition chips to reduce the temperature difference between the data acquisition chips.

The invention also provides a detector assembly and CT system incorporating such a thermal management arrangement, as well as a method based upon such principles.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

Figure 1:
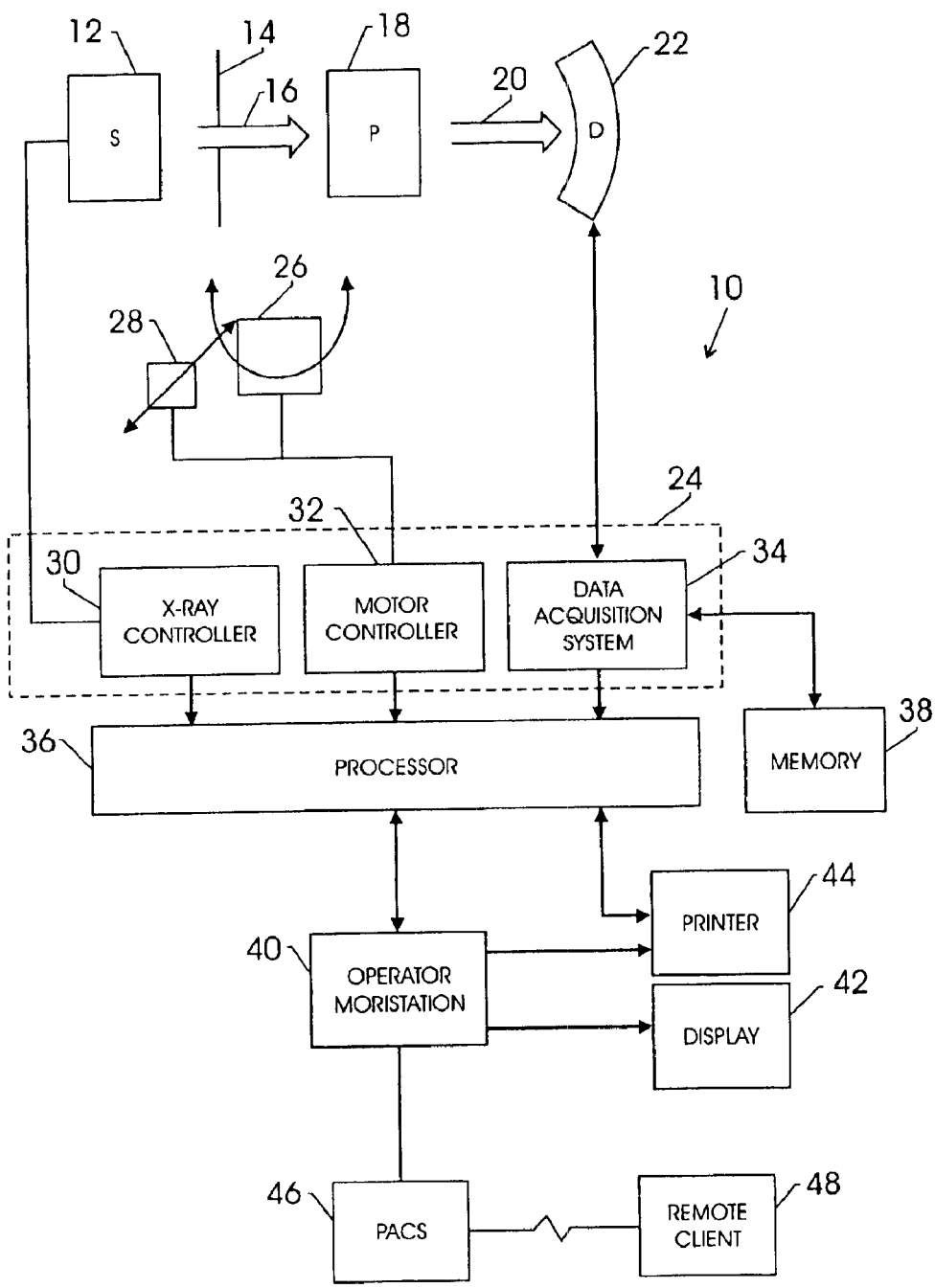
FIG. 1 is a diagrammatical view of an exemplary imaging system in the form of a CT imaging system for use in producing processed images in accordance with aspects of the present technique.

Turning now to the drawings, FIG. 1 illustrates diagrammatically a computed tomography (hereinafter "CT") system 10 for acquiring and processing image data. More particularly, the CT system 10 acquires original image data, and further processes the image data for subsequent display and analysis. In the embodiment illustrated in FIG. 1, the CT system 10 includes a source of X-ray radiation 12 positioned adjacent to a collimator 14. In this exemplary embodiment, the X-ray radiation source 12 is typically an X-ray tube.

The collimator 14 permits an incident X-ray beam 16 to pass into a region in which an object, such as a human patient 18 is positioned. A portion of the radiation 16 passes through or around the object 18 and subsequently the radiation 20 impacts a detector array, represented generally by reference numeral 22. Generally, the detector array 22 detects the X-ray beams 16, 20 and subsequently converts this X-ray radiation to a plurality of electrical signals that represent the intensity of the incident X-ray beam 16. These electrical signals are acquired and processed further to construct an image of the features within the object, for example, the human patient 18.

The X-ray radiation source 12 is controlled by a system controller 24 that furnishes both power, and control signals for CT examination sequences. Moreover, the detector array 22 coupled to the system controller 24 commands acquisition of the signals generated in the detector array 22. In general, the system controller 24 commands operation of the imaging system to execute examination protocols and to process acquired data. Further, referring to FIG. 1, the system controller 24 is coupled to a linear positioning subsystem 26 and a rotational subsystem 28. The rotational subsystem 28 enables the X-ray source 12, the collimator 14 and the detector array 22 to be rotated at least one full 360° turn around the patient 18. It should be noted that the rotational subsystem 28 might include a gantry 54 fixedly attached to the X-ray radiation source 12 and the detector array 22 (see FIG. 2). Thus, the system controller 24 may be utilized to operate the gantry 54 typically around a longitudinal axis. The linear positioning subsystem 26 enables the patient 18, or more specifically a patient table 58, to be displaced linearly. Further, the patient table 58 may be linearly moved within the gantry 54 to generate images of target areas of the object 18.

Additionally, as may be appreciated by those skilled in the art that, the source of X-ray radiation 12 may be controlled by an X-ray controller 30 disposed within the system controller 24. More particularly, the X-ray controller 30 is configured to provide power and timing signals to the X-ray source 12. A motor controller 32 may be utilized to control the movement of the rotational subsystem 28 and the linear positioning subsystem 26. Further, the system controller 24 also comprises a data acquisition system 34. Typically, the detector array 22 is coupled to the system controller 24 and more particularly to the data acquisition system 34. The data acquisition system 34 receives data collected by plurality of electronic circuits building the detector array 22. In operation, the data acquisition system 34 receives sampled analog signals from the detector array 22 and converts them to digital signals for subsequent processing by a processor 36, typically a computer.

Operationally, the processor 36 is coupled to the system controller 24. The data collected by the data acquisition system 34 may be transmitted to the processor 36 and moreover, to a memory 38. It should be understood that any type of memory that stores a large amount of data might be utilized by the exemplary CT system 10. The memory 38 may include remote components for storing data, processing parameters and storing predetermined instructions in form of computer programs. In addition, the processor 36 is configured to receive commands and scanning parameter inputs from an operator via an operator workstation 40 typically equipped with a keyboard and other input devices. An operator may control the CT system 10 via the input devices. Thus, the operator may observe the constructed image and other data relevant to the system from the computer 36, initiate imaging, and so forth.

A display 42 coupled to the operator workstation 40 may be utilized to observe the constructed image and to control imaging process. Additionally, the scanned image may be printed by a printer 44, typically coupled to the operator workstation 40. The display 42 and printer 44 may also be connected to the processor 36, either directly or via the operator workstation 40. Further, the operator workstation 40 may also be coupled to a picture archiving and communications system (hereinafter "PACS") 46. It should be noted that PACS 46 might be coupled to a remote system 48 including, without limitation, radiology department information system (hereinafter "RIS"), hospital information system (hereinafter "HIS") via an internal or an external network, so that users at different locations may gain access to the image and the image data.

Figure 2:
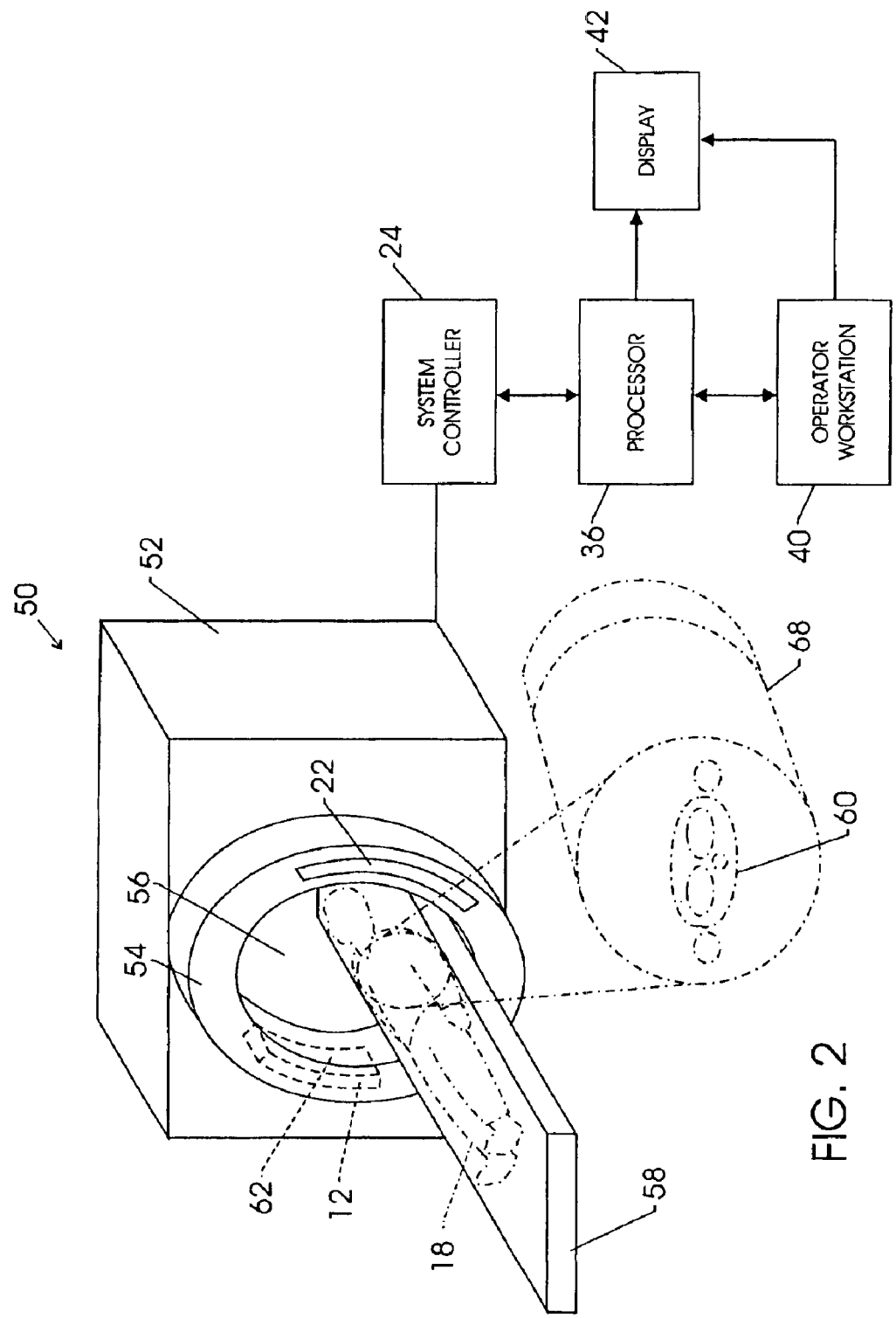
FIG. 2 is diagrammatical view of an exemplary physical implementation of the CT system of FIG. 1.

Referring generally to FIG. 2, an exemplary imaging system utilized in present embodiment may be a CT scanning system 50. The exemplary CT scanning system 50 depicted in FIG. 2 in accordance with aspects of the present technique offers a wider array of axial coverage, relatively higher rotational speed of the gantry 54 and finer spatial resolution compared to conventional CT scanning systems. Constructional aspects of the exemplary CT scanning system 50 in FIG. 2 is illustrated with a frame 52 and the gantry 54 having an aperture 56. Further, the patient table 58 is positioned in the aperture 56 of the frame 52 and the gantry 54. The patient table 58 is adapted so that a patient 18 may recline comfortably during the examination process. Additionally, the patient table 58 is configured to be displaced linearly by the linear positioning subsystem 26 (see FIG. 1).

Figure 3:
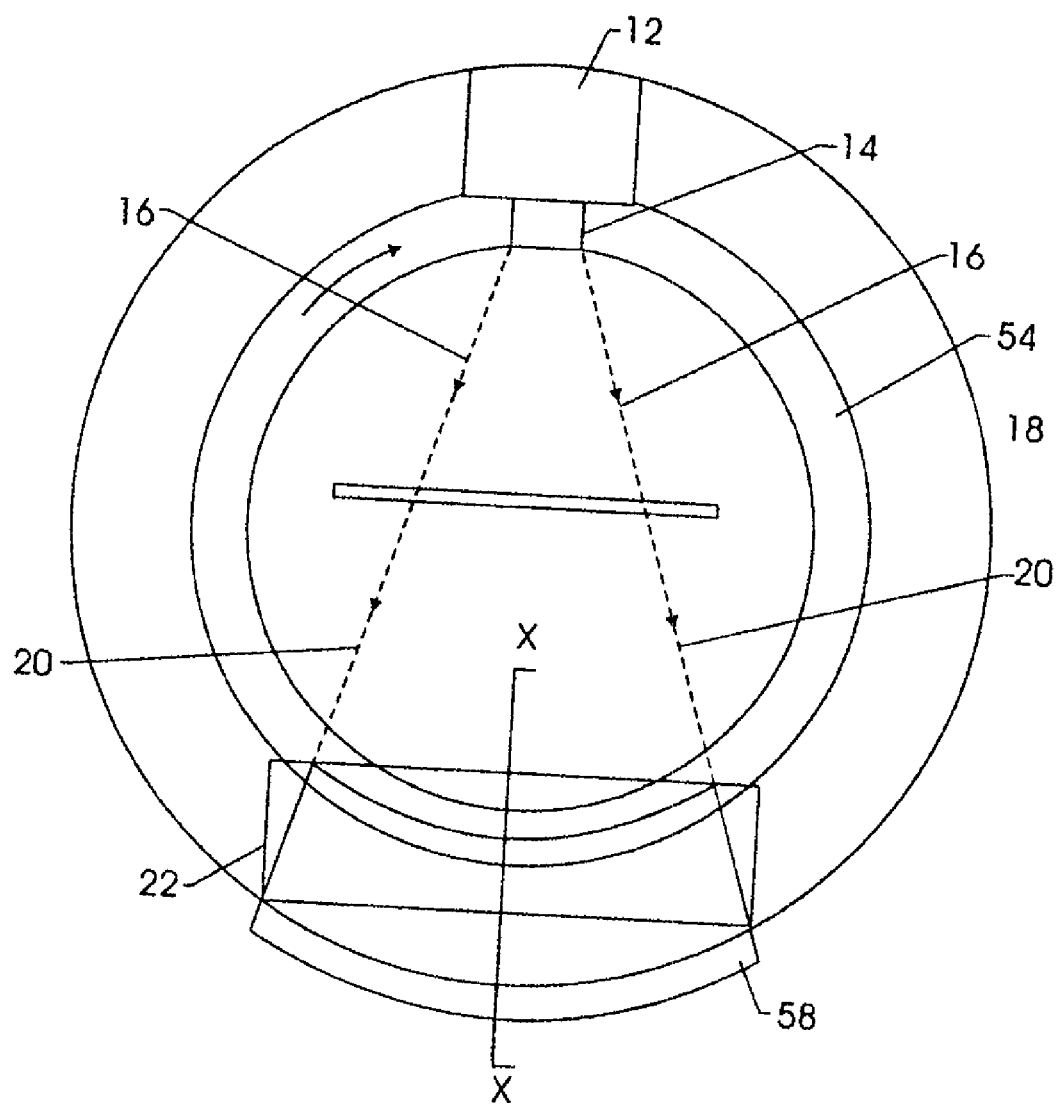
FIG. 3 is a representation of certain of the subsystems of the CT system of FIG. 2, including a radiation source and a detector array for receiving radiation during imaging sequences.
Figure 4:
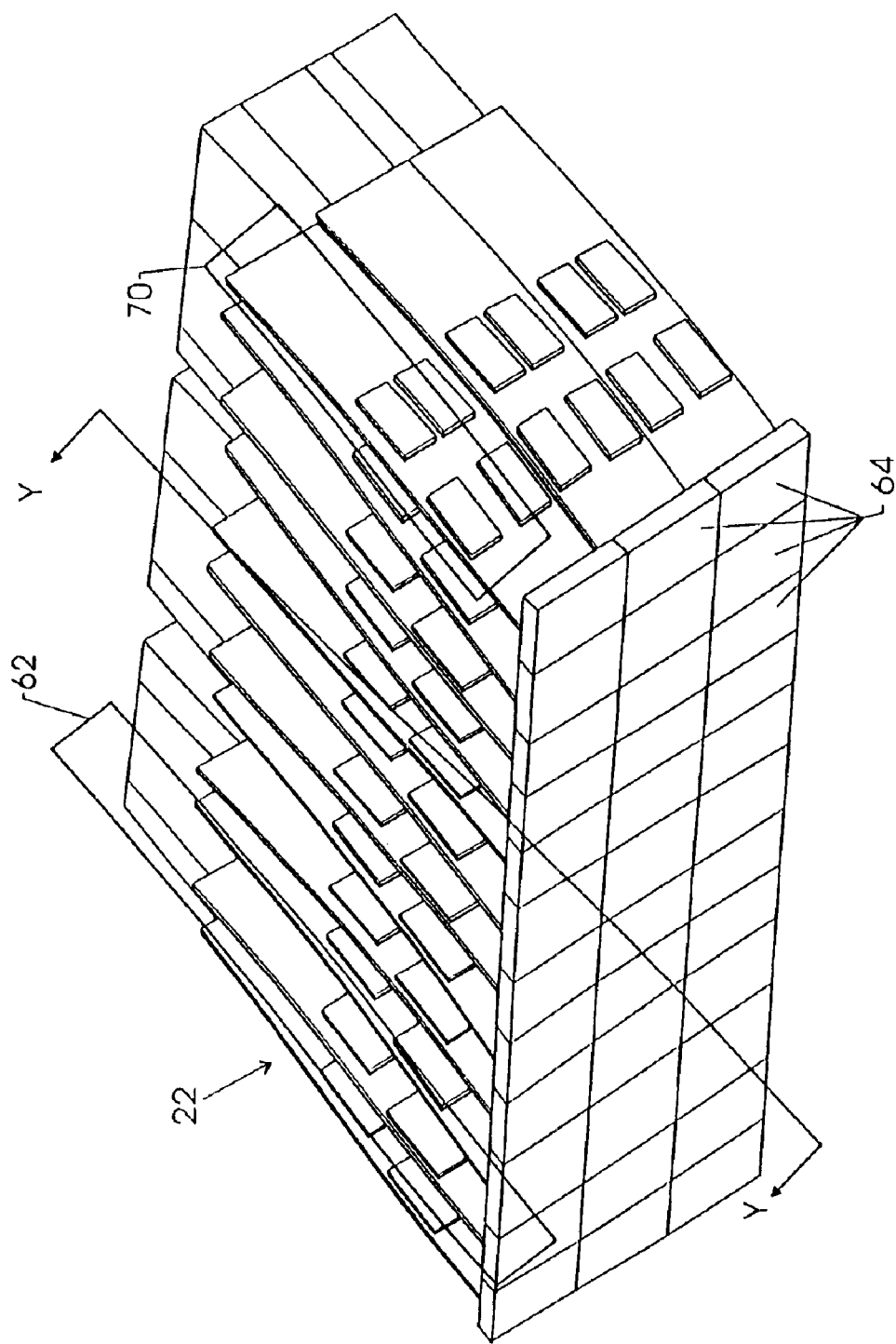
FIG. 4 is a perspective view of series of detector assemblies used in the detector array of FIG. 3, showing an exemplary arrangement of a plurality of detector circuits comprising the detector assembly.
Figure 5:
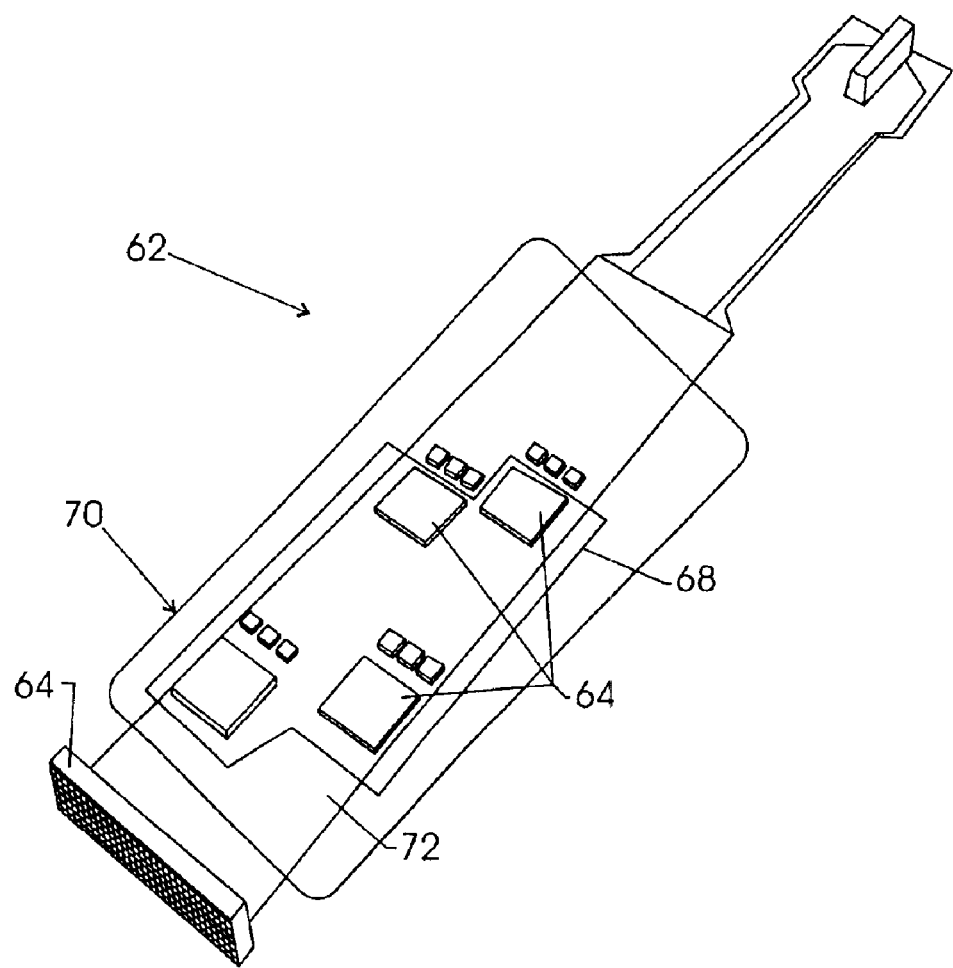
FIG. 5 is a perspective view of an exemplary circuit board assembly FIG. 4, depicting typical constructional aspects of a single detector circuit in accordance with the present technique.

FIG. 3 is a representation of certain of the subsystems of the CT scanning system 50 of FIG. 2. Operationally, the X-ray radiation source 12 projects the X-ray beam 16 towards the object 18, and further towards the detector array 22. As discussed in preceding paragraphs, a portion of the incident X-ray beam 16 passes through or around the object 18 and subsequently a portion of the incident X-ray beam 16 including the attenuated X-ray beam 20 impinges on the detector array 22. An exemplary arrangement of the detector array 22 comprising a plurality of detector assemblies 62 is shown in FIG. 4. Further, FIG. 5 shows typical constructional aspects of each detector assembly 62 in accordance with the present technique. Typically, each of these detector assemblies 62 includes a detector subassembly 64 and at least one circuit board assembly 70 coupled to the detector subassembly 64.

Referring to FIGS. 4 and 5, operationally, each detector subassembly 64 is constructed of a plurality of solid-state detectors and photodiodes attached with each of these detectors (not shown). These solid-state detectors comprise scintillating crystals that fluoresce when struck by X-ray beams to produce light energy there from. Further, these photodiodes transform the light energy into a plurality of electrical signals. Therefore, the detector subassembly 64 is adapted to detect the X-ray beams 16, 20 and further converts these X-ray beams to a plurality of electrical signals. The data corresponding to these electrical signals represents intensity of the X-ray beams 16, 20 at the position of the detector subassembly 64 at the time these X-ray radiations impinge thereon. These data are acquired by the circuit board assembly 70 that includes an integrated circuit array, for example, a data acquisition chip array 68 mounted on at least one printed circuit board 72. More particularly, as the X-ray radiation source 12 and the detector array 22 fixedly attached to the gantry 54 rotate, the integrated circuit array, for example, the data acquisition chip array 68 comprising plurality of integrated circuits, such as, data acquisition system chips 66 mounted on the printed circuit board 72 collect data corresponding to electrical signals that represent attenuation of the incident X-ray beams 16 after passing through or around the object 18. The processor 36 coupled with the data acquisition system 34 is configured to process those data to generate a plurality of projection measurements and further perform computations on those projection measurements to construct an image 60 of the object 18.

It may be understood that a portion of the electrical energy corresponding to the electrical signals acquired by each of these plurality of data acquisition chips 66 is converted to thermal energy. In implementation, the width of each detector assembly 62 of the detector array 22 of the exemplary CT scanning system 50 recited in present technique, is generally larger compared to conventional CT scanning systems to facilitate accommodating wider coverage of the human patient 18. Accordingly, the thermal load generated from each of the data acquisition chips 66 of the detector assembly 62 is substantially higher compared to thermal load generated from detector assemblies of conventional CT systems. Typically, a thermal management system designed in accordance with aspects of present technique mitigates the thermal load generated from each of the detector assemblies 62 of the CT scanning system 50. Further, this thermal management system facilitates control of the thermal environment of each detector assembly 62, and maintenance of the chips in a relatively isothermal condition (i.e. minimizing temperature differences between the chips).

Figure 6:
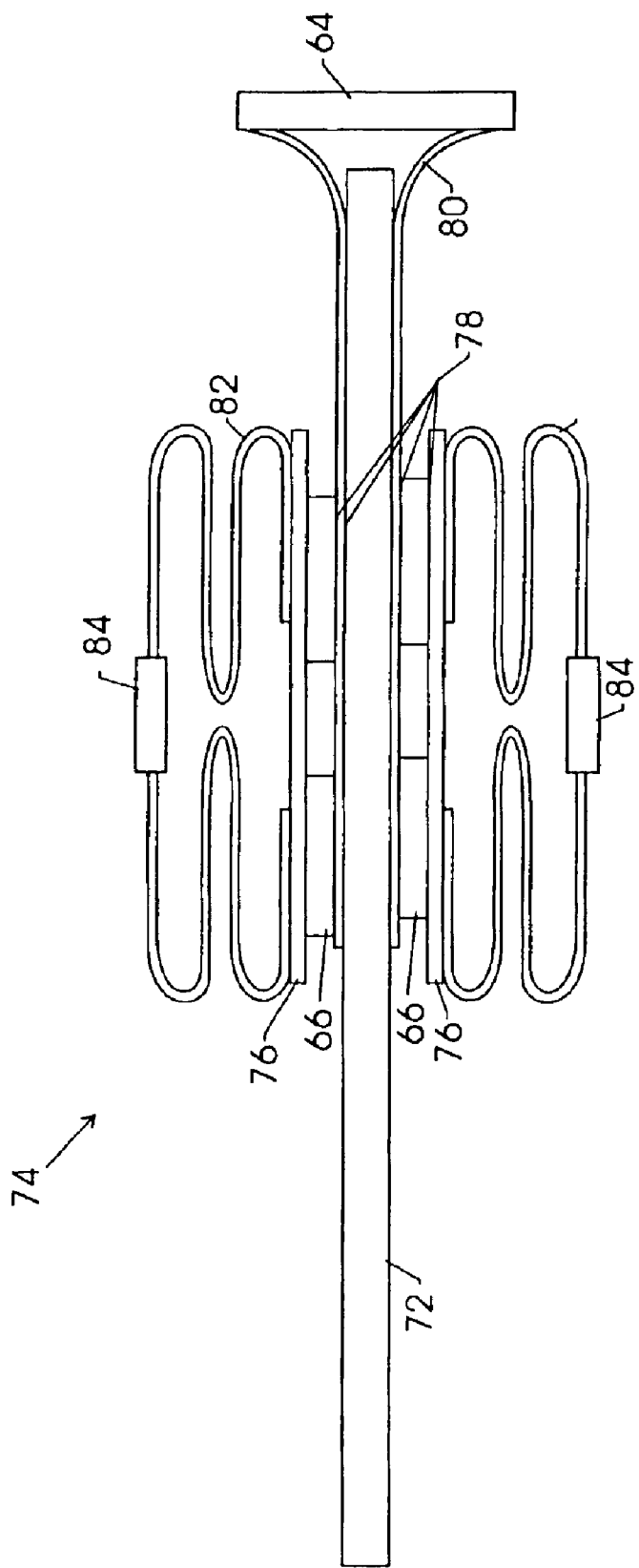
FIG. 6 is a side elevational view of the thermal management system for data acquisition system (DAS) circuit chips of the type used in the detector circuitry of FIG. 5.
Figure 7:
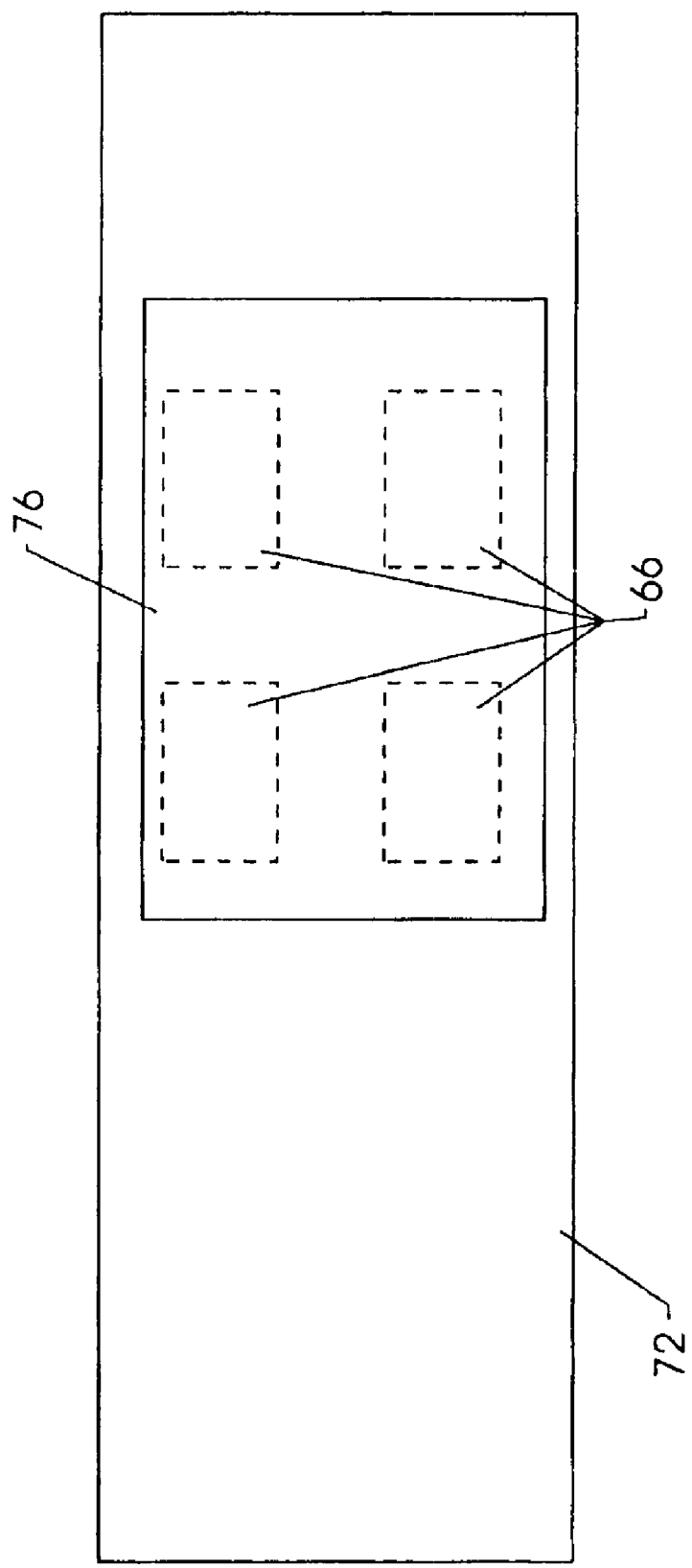
FIG. 7 is a plan view of an exemplary board assembly of the type included in the system of FIG. 6, on which DAS chips are mounted.

One embodiment of a thermal management system in accordance with the present technique is illustrated in FIG. 6. The system, described in greater detail below, includes a subassembly illustrated in FIG. 7. At its best, the technique may be based upon the arrangement of FIG. 7 and obtain certain of the inventive benefits, with or without additional structures of the type show in FIG. 6. Referring specifically to the embodiment of FIG. 7, in some embodiments, this thermal management system includes a heat sink assembly, which may take the form of a spreader plate 76 disposed on two or more data acquisition chips 66, maintaining direct thermal contact therewith. The spreader plate 76 is attached to data acquisition chips 66 by a bonding agent, which may be a thermal adhesive. The spreader plate 76 typically distributes the thermal energy generated by the data acquisition chip array over the circuit board assembly to enable substantially isothermal temperature distribution across entire detector assembly 62. As used herein, the term substantially isothermal temperature distribution means little or insignificant variation in temperature distribution across the detector assembly components, such as, for example, the detector subassembly, the circuit board assembly and the DAS chips 66. The spreader plate may be manufactured from suitable material including but not limited to copper and aluminum. In the exemplary embodiment as shown in FIG. 7, a regular arrangement of DAS chips 66 is formed on the printed circuit board 72. It should be appreciated that several other different arrangements of DAS chips 66 on the printed circuit board 72 may be possible including, but not limited to a staggered arrangement. In the staggered arrangement, DAS chips 66 are disposed diagonally opposite to each other (see FIG. 5) to enhance uniform distribution of thermal energy from the DAS chips 66 to the spreader plate 76.

In a conventional convective cooling of chips in absence of any heat sink arrangement, such as a spreader plate, the temperature of individual data acquisition chips 66 may vary widely. In a specific embodiment, the temperature of the DAS chips may vary from about 62° C. to about 67° C. In one of the disclosed embodiments as shown in FIG. 7, the thermal energy generated in the data acquisition chips 66 is evenly distributed to create substantially isothermal temperature distribution between the individual data acquisition chips 66, over the circuit board assembly 70, and improved thermal management of in the detector subassembly. In operation, the absolute temperatures of such individual chips 66 are configured to be kept below a specified maximum temperature. A substantial drop in the absolute temperature of the individual data acquisition chips was also found when the spreader plate is in direct thermal contact with the chips. In implementation, a heat sink comprising a spreader plate reduces the temperature of the photodiodes (not shown) as the heat is transferred from the DAS chips 66 into the ambient. The convective heat transfer from the heat sink to the ambient may be achieved by blowing a cooling medium, such as, air through one or more blowers disposed in a plenum (not shown). The cooling air is typically the ambient air inside the gantry 54.

Furthermore the variation in temperature in the individual DAS chips is substantially lower as the spreader plate 76 enhances isothermal temperature distribution between the DAS chips array 68. The reduction in variation of temperature between individual DAS chips 66, and the subsequent reduction in the temperature of the detector assembly 62 enhance the service life, reliability, and performance of the chips and the overall system, reflected ultimately in the quality of images produced by a CT system.

In an exemplary embodiment, as mentioned above, the spreader plate 66 is further connected to a heat dissipation arrangement, as shown in FIG. 6. The heat dissipation device may comprise plurality of fins 82 to enhance heat transfer from the DAS chips 66. One construction of such fins is depicted in an exemplary embodiment shown in FIG. 6. The fins 82 may be directly in thermal contact with the spreader plate 76 where they can be attached with the spreader plate using high conductivity adhesive that has high bonding strength. It may be noted that, the surface area of the fins 82 may be adjusted by selecting their cross-sectional geometry from various configurations that include, but are not limited to, square-shaped geometry, rectangular-shaped geometry, circular-shaped geometry, elliptical-shaped geometry and irregular-shaped geometry.

In one embodiment the fins 82 are irregularly shaped as shown in FIG. 6. These are spring type fins 82 made from flat metal sheets with thickness of about 0.125 mm to about 0.5 mm. The fins 82 may be made from metals including, but not limited to beryllium-copper, copper and aluminum. Flat spring type fins 82 may be formed by folding the thin metal sheets in preheated condition. Two such fins 82 can be placed on the heat spreader adjacent to each other. When the fins have an irregularly shaped geometry, the open ends may cause vibration, which can be prevented by inserting the ends of the fins in a slotted block 84. The block 84 could be made of any plastic material. The blocks may further be connected to one or more protective devices (not shown), which essentially connect the fin structures to the printed wire boards. These structures are configured to release the strain generated in the DAS chips due to vibration of the fin structure while the CT system is in operation. The fins 82 and the block 84 are designed in such a fashion as to minimize the weight on the DAS chips 66, while providing the desired thermal management benefits. The mass of the spreader plate is further optimized to achieve the desired thermal dampening affect to reduce fluctuation of temperature in the DAS chips.

In a present embodiment, the DAS chips 66 are attached to the spreader plate using a flexible material 78 such as Kapton. The circuit board assembly 70 is also connected to the detector subassembly 64 through the same flexible material. The circuit board assembly 70 is physically adjacent to the detector subassembly 64 in the exemplary embodiment depicted in FIG. 6, which ensures thermal communication between these two elements.

Figure 8:
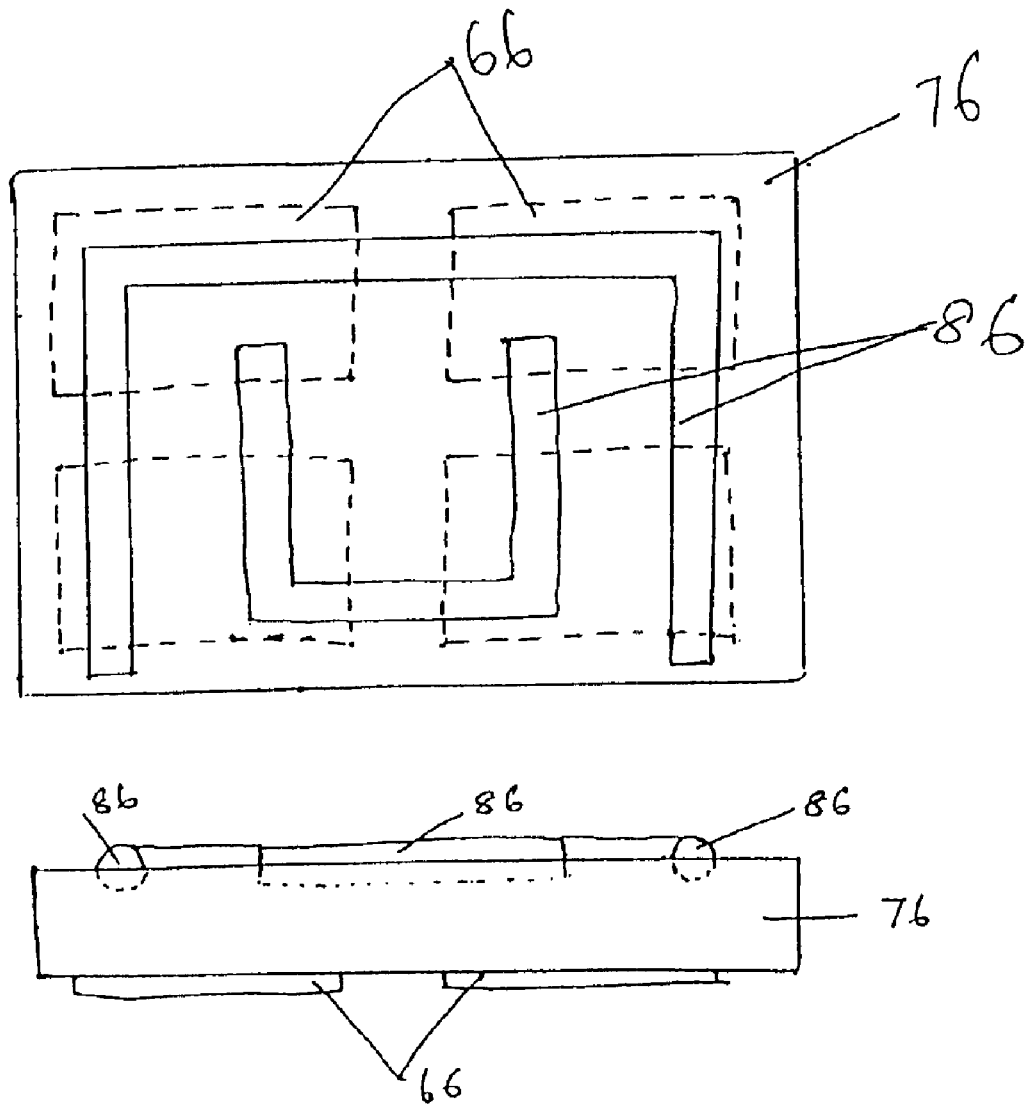
FIG. 8 includes plan and elevational views of an exemplary spreader plate arrangement for use in a DAS chip thermal management system connected to heat pipe.

In one embodiment the heat sink further comprises one or more heat pipes 86 embedded on the spreader plate 76 as shown in FIG. 8. In operation, these heat pipes are typical passive heat transfer devices driven by thermal load of a heat source, viz. the data acquisition chip array 68 and transfer thermal energy from this heat source (i.e. the data acquisition chip array 68) to the heat sink assembly 76 based upon two-phase heat transfer principles. Generally, each of these heat pipes 86 typically includes a closed evacuated chamber fabricated from a thermally conductive material, for example, copper. Further, inner surfaces of the chamber are lined with typical wick structure having capillary properties and these wick structures are saturated with a working fluid. Thermal energy at a higher temperature end of the heat pipe (also referred as evaporator section) vaporizes the working fluid within portion of the wick structure exposed to the evaporator section. Subsequently, the vaporized working fluid transfers its latent heat of vaporization to the heat sink assembly 76. The condensed working fluid is drawn back to the evaporator section of those heat pipes by capillary action of the wick structure.

This mechanism enhances the heat dissipation from the spreader plate to the ambient by blowing air from one or more air blowers (not shown). The heat pipes 86 are constructed from material with high conductivity to enhance the conductive heat transfer from the spreader plate 76 to the heat pipes 86. The working fluid used in the heat pipe is selected based on the compatibility of the fluid with the material of construction of the heat pipes and the wick material. The working fluid used for this technique includes but is not limited to solvents. In one embodiment water may also be used the working fluid. The design of the arrangement of the heat pipes 86 on the spreader plate 76 as depicted in FIG. 8 is an exemplary arrangement. It may be possible to design the arrangement of the heat pipe in several different arrangements to enhance the cooling of DAS chips 66.

Figure 9:
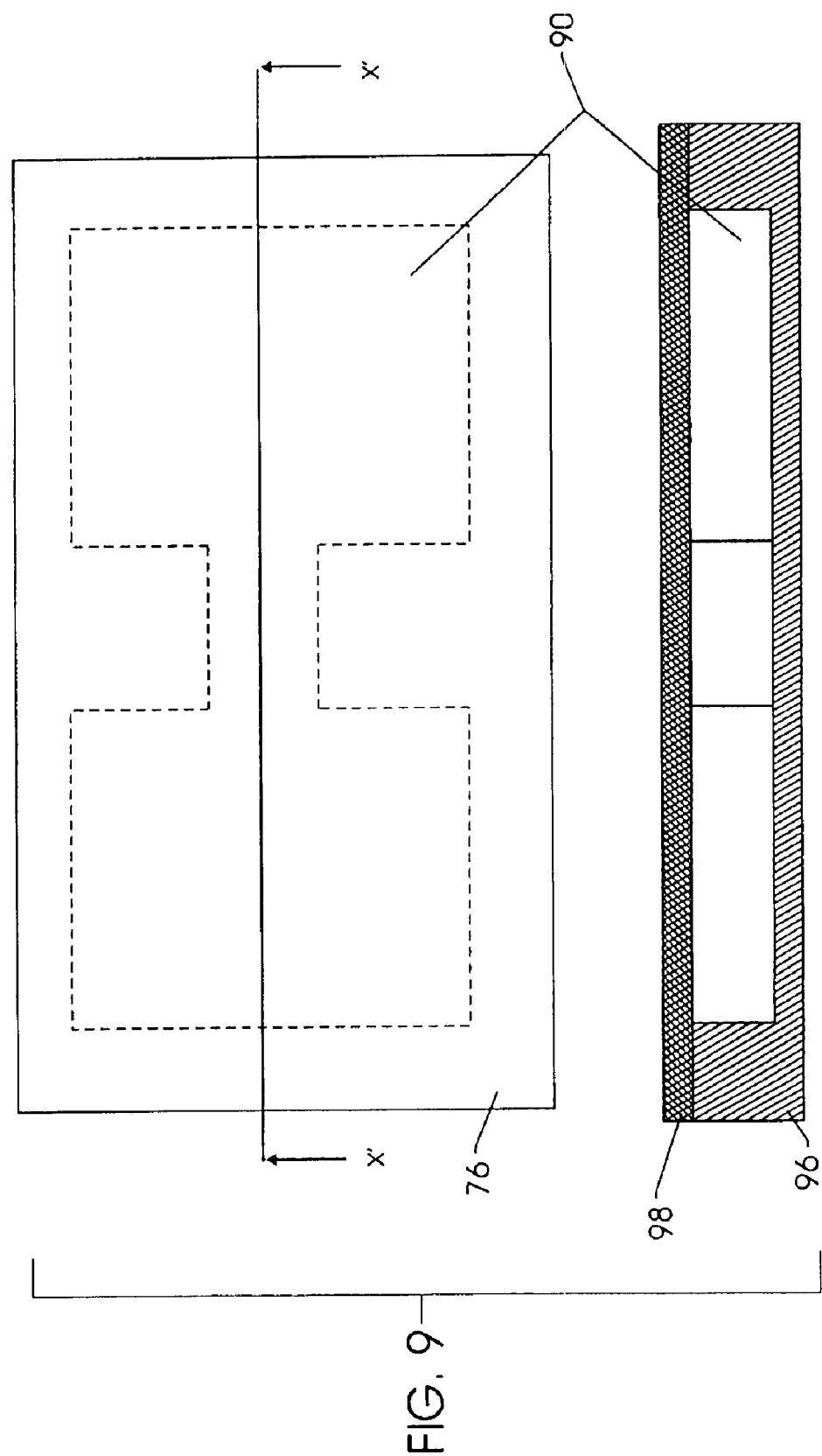
FIG. 9 includes plan and sectional views of an alternative spreader plate arrangement.
Figure 10:
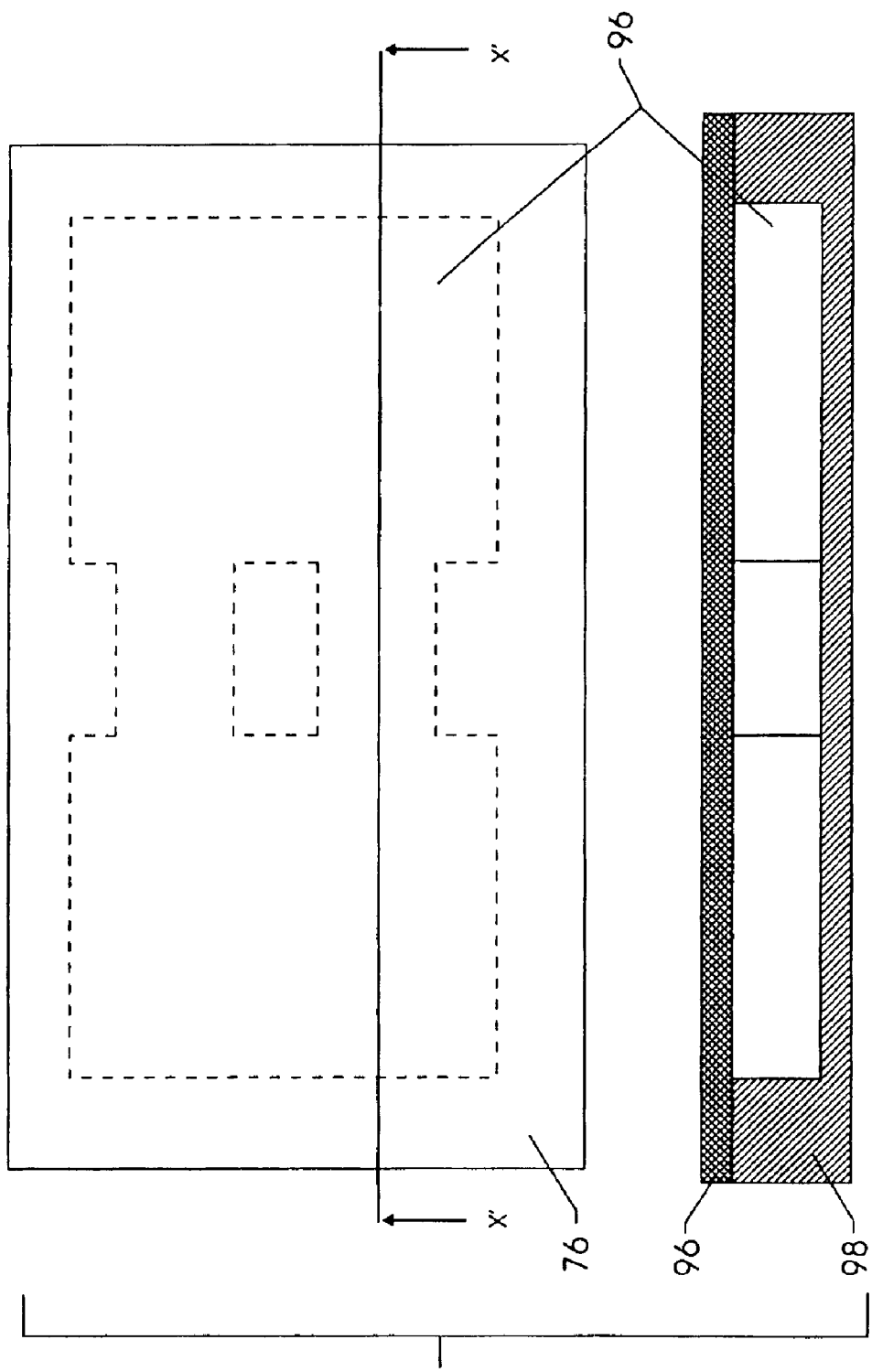
FIG. 10 includes plan and sectional views of a further alternative spreader plate arrangement.

In some embodiments the spreader plate 76 may be configured to have one or more hollow interior section as shown in FIGS. 9 and 10. The hollow sections (also called vapor chamber) 90 may be filled with wire mesh (not shown), which may further contain a heat transfer fluid. The spreader plate 76 may further comprise two sections, including a top section 98 and a bottom section 96. The bottom section 96 is attached to the DAS chips 64 (not shown in FIGS. 9 and 10). In operation, the thermal energy is transferred to the spreader plate 76, the heat transfer fluid is heated and reaches a boiling point. The latent heat of vaporization is supplied by the thermal energy flowing from the DAS chips 64 to the spreader plate 76. As the vapor flows upward inside the vapor chamber 90, the vapor is cooled and, while condensing releases the latent heat at the top surface 98. The heat is then dissipated from the top surface 98, which is enhanced by the air circulation through one or more air blowers (not shown). In another embodiment the heat dissipation process may further be enhanced by a plurality of fins (not shown) attached to the top surface 98 of the spreader plate 76. The heat transfer fluid used for this embodiment may include but not limited to solvents. In one embodiment water may also be used as the heat transfer fluid.

Figure 11:
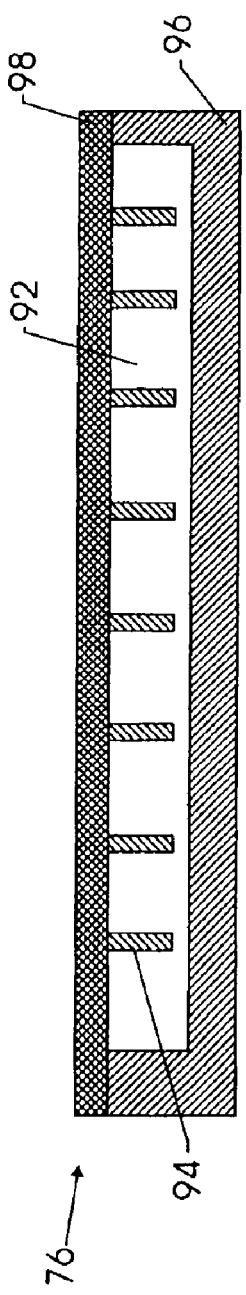
FIG. 11 is a sectional view of another alternative spreader plate filled with phase change material.
Figure 12:
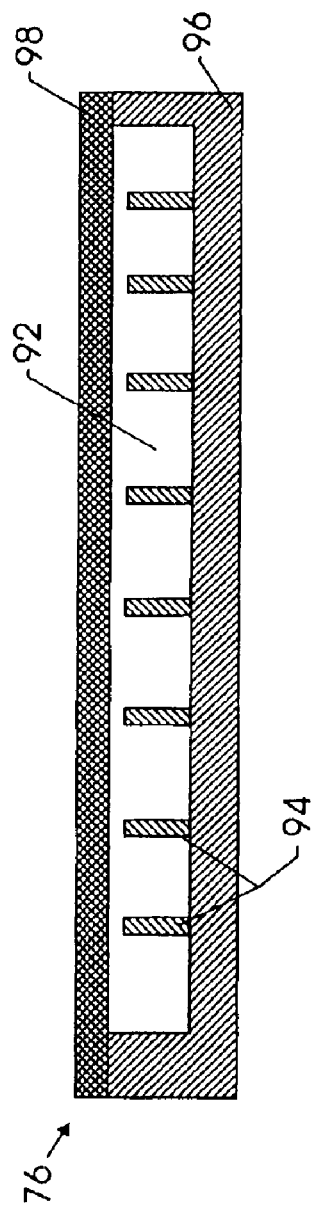
FIG. 12 is a sectional view of another alternative embodiment of a spreader plate filled with phase change material.
Figure 13:
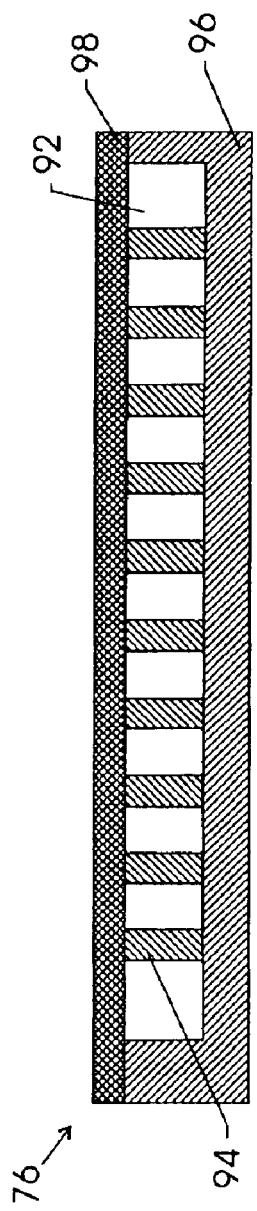
FIG. 13 is a sectional view of another embodiment of a spreader plate filled with phase change material.
Figure 14:
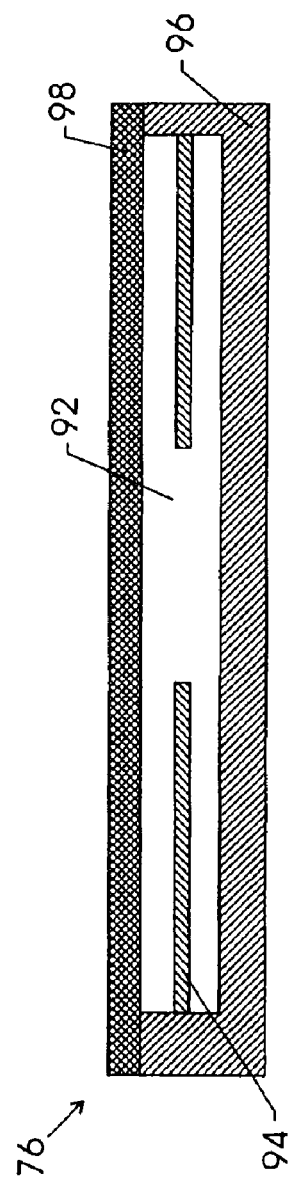
FIG. 14 is a sectional view of still another embodiment of a spreader plate filled with phase change material.

In some embodiments the spreader plate 76 is configured to have one or more hollow interior sections 92, which contain a phase change material (herein after PCM) as shown in FIGS. 11, 12, 13 and 14. In one embodiment the spreader plate 76 has a top section 98 and bottom section 96 as shown in FIG. 11. The hollow interior 92 of the spreader plate 76 is filled with PCM. The spreader plate 76 is in thermal communication with the DAS chips 66. In operation the thermal energy generated by the DAS chips 66 is conducted to the spreader plate 76. As a result, the energy is transmitted to the PCM filled hollow section 92. PCM, which is typically a solid material, begins to melt, and the latent heat of fusion is supplied by the conducting the thermal energy flowing from the DAS chips 66. The heat conduction from the DAS chips 66 to the spreader plate 76 is further enhanced by the conductive elements 94, which are configured to be attached to the bottom section 96 in one embodiment as shown in FIG. 11, or in another embodiment to the top section 98 of the spreader plate 76 as shown in FIG. 12. These conducting elements 94 may be strips or fins made from metal of high conductivity. Several other configurations of the conducting elements are possible, including but not limited to the configurations shown FIG. 13 and FIG. 14. In FIG. 13 the spreader plate 76 is attached to conducting elements 94, which are attached to both the bottom section 96 and the top section 98. In FIG. 14 the conductive elements are attached to the sides of the bottom section 96 of the spreader plate 76.

At any time when the CT system is in operation the thermal energy released from the DAS chips 64 increases, thereby melting the PCM, which is present in the hollow interior 92 of the spreader plate 76. The latent heat of fusion is supplied by the thermal energy released by the DAS chips 64, which is conducted through the bottom section 96 of the spreader plate 76 into the PCM. In this process the DAS chips 66 are cooled, thereby reducing the temperature of the detector subassembly 64. When the CT system is not in operation, the thermal energy stored in the PCM is released and the PMC solidifies releasing the latent heat. As described in the preceding embodiments, the phase change material maintains near isothermal condition in the DAS chips during the transient periods when the gantry rotates and imaging is in progress. The thermal management system, as depicted in FIGS. 11, 12, 13 and 14, using phase change material, may further be enhanced by a plurality of fins (not shown) made of metals of high conductivity, which are configured to be attached to the spreader plate 76.

The phase change material (PCM) is chosen from a wide range of compounds including, but not limited to, organic compounds of n-alkane series, paraffin waxes, hydrated salts and low melting point alloys. The melting point of the PCM can be designed to suit the particular requirement of cooling of the DAS chips 64 depending on the design of the CT system.

Figure 15:
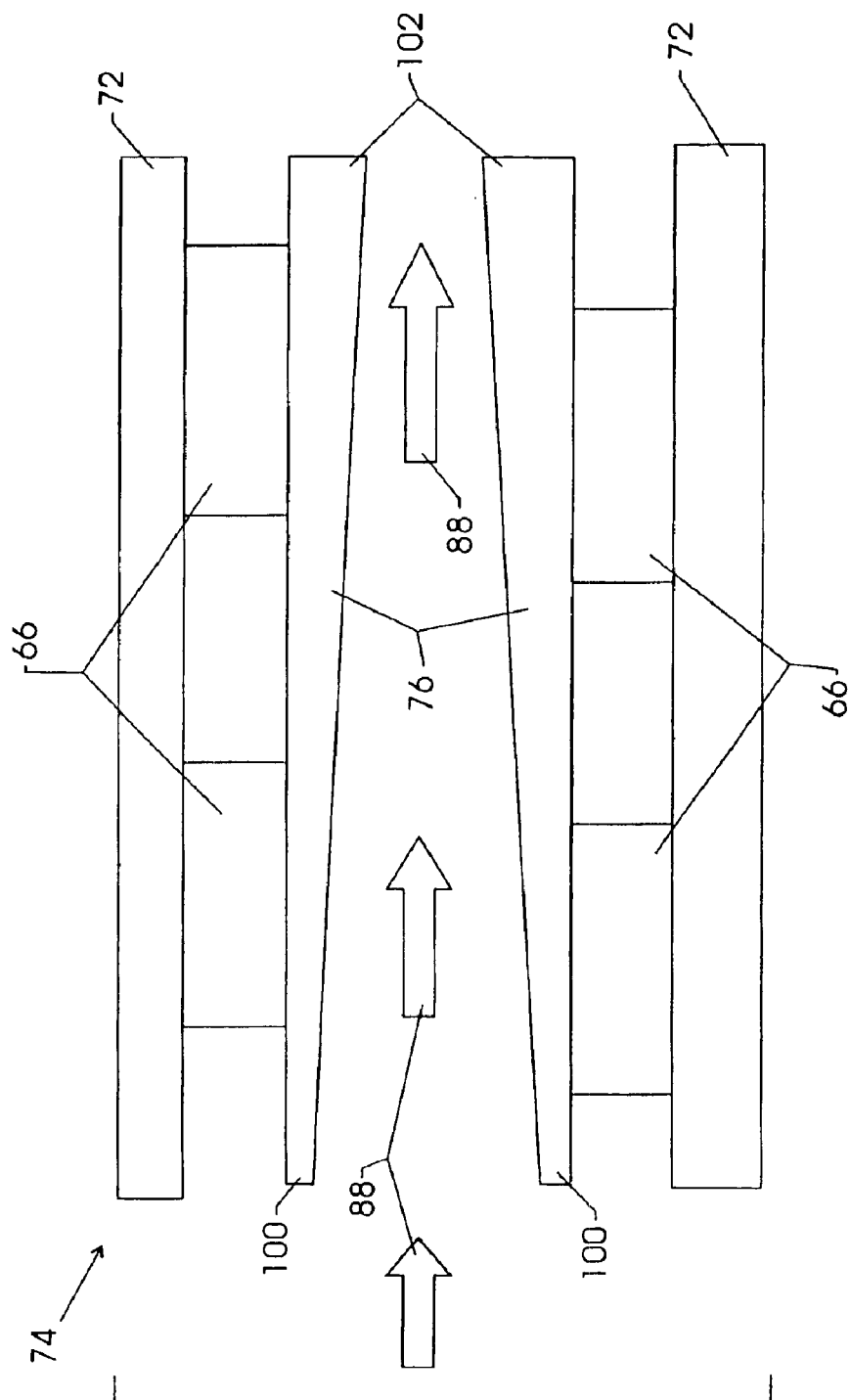
FIG. 15 is a diagrammatical elevational view of an alternative thermal management system of DAS chips.

In one embodiment the spreader plate 76 is configured to have a wedge-shaped or tapered design as shown in FIG. 15. FIG. 15 shows a thermal management system 74. In the diagrammatical view of FIG. 15 two circuit boards 70 are depicted. The DAS chips 64 are attached to the printed circuit board 72. The spreader plate 76 is configured to have two edges, a leading edge 100 and a trailing edge 102. The thickness of the spreader plate 76 decreases along the length of the spreader plate from the leading edge 100 to the training edge 102. The path of the airflow 88 for convective cooling is shown along the length of the spreader plate 76. As the thickness of the spreader plate 76 increases along with the path of the airflow 88 as shown in FIG. 15, the cross-sectional area to the airflow gradually decreases accordingly. In operation this creates an increase in the velocity of the air as it travels along the length of the spreader plate 76. The temperature of the air, when it comes in contact with the leading edge 100, is lower than the temperature of the air at the trailing edge 102. This is due to the fact that as the air travels along the length of the spreader plate 76, thermal energy is dissipated into the air thereby raising the air temperature. In order to maintain an uniform temperature in the DAS chips 66 and to avoid any hot spot generation in the spreader plate 76 this increase in air temperature is compensated by the increase in velocity of the air, as the convective heat transfer phenomenon is proportional to the velocity of the heat removing medium, which is air in this exemplary embodiment.

Figure 16:
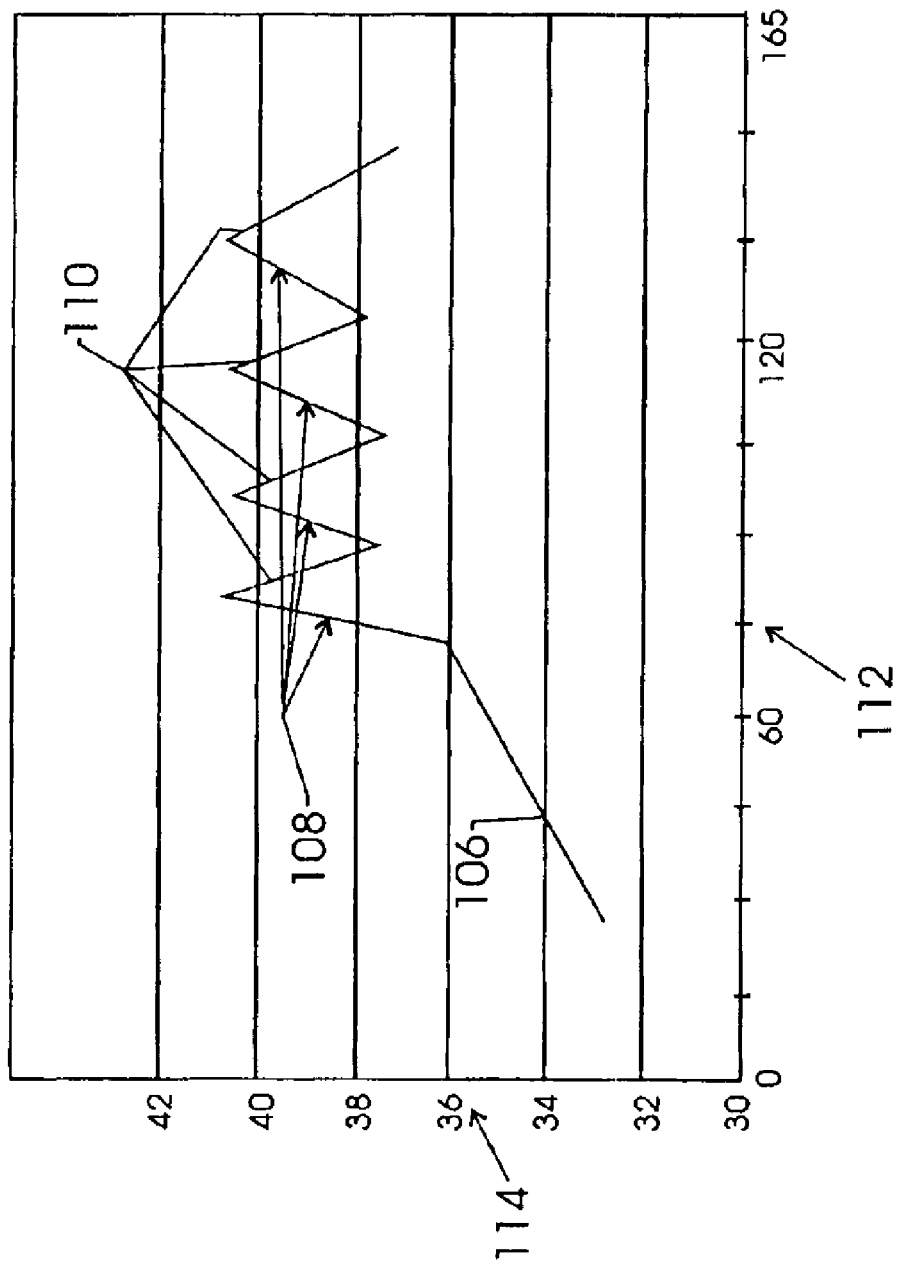
FIG. 16 is a graphical representation showing the temperature profile of the air in the gantry of a CT system employing the present thermal management system over time.

In all embodiments, as described in the preceding sections, the convective cooling medium is the ambient air inside the gantry. FIG. 16 is a graph, which shows the exemplary temperature change in the ambient inside a CT system. In the graph, the X axis 112 shows the time of a day in minutes and Y axis 114 shows the temperature of the air inside the gantry 54. The temperature of the air inside the gantry is kept under a certain maximum temperature, which is determined by the design of the CT system. The temperature profile of the ambient air inside the gantry has several sections. Section 106 shows the gradual increase in the air temperature as the detector assembly is powered on. Sections 108 show the scanning mode, during which a steep increase in the air temperature is observed. This rise in temperature is attributed to the heat generated by the X-ray source while the imaging process is underway. After the scanning mode, the gantry stops rotating and the temperature falls as shown in the sections 110. This phase is typically called "park mode" when the gantry is in a stationary position. FIG. 16 shows several such cycles of scanning mode as represented by sections 108 and parking mode represented by sections 110. The thermal management system as described in various embodiments as disclosed in the preceding sections, is designed to handle the heat load generated during the scanning and the parking modes of the CT system. Moreover, the thermal management system, as described in various embodiments as disclosed in the preceding sections, is also configured to keep the DAS chips in a substantially isothermal condition in the transient periods while the ambient air temperature increases or decreases (as shown in FIG. 16), as well as while thermal transfer conditions change (e.g. by increase or decrease in convective heat transfer during the scanning mode in a CT system), and as heat loads change during operation of the circuitry. For such temporal changes in conditions, the system operates as a thermal damper for temperature variations over time.

The embodiments described above, depicts the thermal management system of a detector assembly of a CT scanner system. The main advantages of the disclosed embodiments include the ability to keep the data acquisition chips in a substantially isothermal condition and to dissipate thermal energy generated in a detector assembly. The heat dissipation process brings down the temperature of the data acquisition chips and subsequently cools the detector assembly. The near isothermal condition in the data acquisition chips and cooling of the DAS chips and subsequently the detector assembly enhance the image quality as well as provide an opportunity for building additional flexibility for the CT scanning system design, such as, enhancing system reliability while operating these scanning systems at wider operating temperature ranges.

While the invention may be susceptible to various modifications and alternative forms, specific embodiments have been shown by way of example in the drawings and have been described in detail herein. However, it should be understood that the invention is not intended to be limited to the particular forms disclosed. Typically, the thermal management system envisioned in accordance with the present technique may as well be utilized in electronic circuits for other systems including medical imaging systems, such as, X-ray imaging system and magnetic resonance imaging system, for example. Accordingly, the invention in its present form is intended to cover all modifications, equivalents, and alternatives falling within the spirit and scope thereof as defined by the following appended claims.

What is claimed is:

1. A computed tomography system comprising:
   a gantry configured to rotate around a longitudinal axis;
   an X-ray radiation source secured to the gantry and configured to project a plurality of X-ray beams through an object;
   a detector array secured to the gantry and comprising a plurality of detector assemblies configured to produce a plurality of electrical signals corresponding to the X-ray beams; each detector assembly further comprising a detector subassembly and at least one circuit board assembly mechanically secured to the detector subassembly via a flexible connection, each circuit board assembly comprising a plurality of integrated circuits attached to at least one printed circuit board and a thermal management system in thermal communication with the integrated circuits to reduce variation in temperature in each of the detector assembly, each thermal management system including a heat sink assembly comprising a substantially rigid thermally conductive spreader plate disposed over two or more integrated circuits to uniformly distribute the thermal energy generated by the integrated circuits during operation; and
   a processor configured to process the electrical signals to generate a plurality of projection measurements, wherein the processor is configured to perform calculations on the projection measurements to construct an image of the object there from.

2. The computed tomography system according to claim 1, wherein the detector subassembly is in thermal communication with the circuit board assembly.

3. The computed tomography system according to claim 2, wherein the circuit board assembly is physically adjacent to the detector subassembly.

4. The computed tomography system according to claim 1, wherein the thermal management system is configured to transfer heat from the integrated circuits to the heat sink assembly.

5. The computed tomography system according to claim 1, wherein the heat sink assembly further comprises at least one heat dissipation system to perform free convective thermal exchange with the thermal energy transformed from the spreader plate.

6. The computed tomography system according to claim 5, wherein the heat dissipation system comprises a plurality of fins adapted to perform convective heat dissipation of the thermal energy transported therein from the integrated circuits.

7. The computed tomography system according to claim 6, wherein the fins are made of material chosen from the group consisting of beryllium-copper, copper and aluminum.

8. The computed tomography system according to claim 6, wherein the fins are attached to the spreader plate through adhesives of high conductivity and high bonding strength.

9. The computed tomography system according to claim 6, wherein the fins are made of sheets of thickness of about 0.1 mm to about 0.5 mm.

10. The computed tomography system according to claim 6, wherein each of the fins has a cross-sectional geometry selected from the group consisting of square-shaped geometry, rectangular shaped geometry, circular shaped geometry, elliptical-shaped geometry and irregular-shaped geometry.

11. The computed tomography system according to claim 6, wherein one end of each of the fins is connected to a block.

12. The computed tomography system according to claim 11, wherein the block is made of plastics.

13. The computed tomography system according to claim 1, wherein the heat sink assembly further comprises at least one conductive heat pipe; the heat pipe being in thermal communication with the spreader plate.

14. The computed tomography system according to claim 13, wherein each heat pipe carries a heat exchange fluid.

15. The computed tomography system according to claim 1, wherein the spreader plate has one or more hollow interior sections.

16. The computed tomography system according to claim 15, wherein the hollow interior section is filled with a wire mesh and a heat exchange fluid.

17. The computed tomography system according to claim 16, wherein the heat exchange fluid is water.

18. The computed tomography system according to claim 16 wherein the spreader plate comprises a top section and a bottom section.

19. The computed tomography system according to claim 18, wherein the top section and the bottom section are connected to conducting elements; wherein the conducting elements are in thermal communication with the top section and the bottom section.

20. The computed tomography system according to claim 15, wherein the hollow interior section is filled with a phase change material.

21. The computed tomography system according to claim 20, wherein the phase change material is chosen from the group consisting of n-alkanes, paraffin waxes, hydrated salts and alloys.

22. The computed tomography system according to claim 1, wherein the spreader plate is configured to have a leading edge and a trailing edge.

23. The computed tomography system according to claim 22, wherein the spreader plate is tapered from the leading edge to the trailing edge.

24. A detector array of a computed tomography system comprising:

a plurality of detector assemblies configured to produce a plurality of electrical signals corresponding to the X-ray beams; each detector assembly further comprising a detector subassembly and at least one circuit board assembly mechanically secured to detector subassembly via a flexible connection, each circuit board assembly comprising a plurality of data acquisition chips attached to at least one printed circuit board and a thermal management system in thermal communication with data acquisition chips to reduce the variation in temperature in the detector assembly, each thermal management system including a heat sink assembly comprising a substantially rigid thermally conductive spreader plate disposed over two or more integrated circuits to uniformly distribute the thermal energy generated by the integrated circuits during operation.

25. The detector array according to claim 24, wherein the detector subassembly is in thermal communication with the circuit board assembly.

26. The detector array according to claim 25, wherein the circuit board assembly is physically adjacent to the detector subassembly.

27. The detector array according to claim 24, wherein the thermal management system is configured to transfer heat from the data acquisition chips to the heat sink assembly.

28. The detector array according to claim 24, wherein the heat sink assembly further comprises at least one heat dissipation system to perform free convective thermal exchange with the thermal energy transformed from the spreader plate.

29. The detector array according to claim 28, wherein the heat dissipation system comprises a plurality of fins adapted to perform convective heat dissipation of the thermal energy transported therein from the data acquisition chips.

30. The detector array according to claim 24, wherein the spreader plate has one or more hollow interior sections.

31. The detector array according to claim 30, wherein the hollow interior section is filled with a wire mesh and a heat exchange fluid.

32. The detector array according to claim 31, wherein the heat exchange fluid is water.

33. The detector array according to claim 30, wherein the hollow interior section is filled with a phase change material.

34. The detector array according to claim 33, wherein the phase change material is chosen from the group consisting of n-alkanes, paraffin waxes, hydrated salts and alloys.

35. The detector array according to claim 24, wherein the spreader plate is configured to have to have a leading edge and a trailing edge.

36. The detector array according to claim 35, wherein the spreader plate is tapered from the leading edge to the trailing edge.

37. A method for controlling thermal environment of a detector array of a computed tomography system comprising:

detecting a plurality of signals emitted from an X-ray radiation source by a detector subassembly;

converting at least a portion of the X-ray beams to a plurality of electrical signals by the detector subassembly;

acquiring data corresponding to the electrical signals by a plurality of data acquisition chips disposed on a circuit board assembly mechanically secured to the detector subassembly via a flexible connection;

generating thermal energy from the data acquisition chips;

distributing the thermal energy uniformly from the data acquisition chips to a heat sink assembly comprising at least one substantially rigid thermally conductive spreader plate over two or more data acquisition chips, the spreader plate being configured to be in thermal communication with the data acquisition chips;

reducing the temperature variation in the data acquisition chips; and dissipating the thermal energy transported to the heat sink assembly from the data acquisition chips by a heat dissipation system.

38. The method according to claim 37, wherein the heat dissipation system is configured to perform free convective thermal exchange with the thermal energy transformed from the spreader plate.

39. A means for controlling thermal environment of a detector array of a computed tomography system comprising:

means for detecting a plurality of X-ray beams emitted from an X-ray radiation source;

means for converting the X-ray beams to a plurality of electrical signals;

means for acquiring data corresponding to the electrical signals;

means for generating thermal energy from a plurality of data acquisition chips mechanically secured to the means for acquiring data via a flexible connection; and means for uniformly distributing the thermal energy from the data acquisition chips to a heat sink assembly comprising a substantially rigid spreader plate.

40. A detector array of a computed tomography system comprising:

a plurality of detector assemblies configured to produce a plurality of electrical signals corresponding to the X-ray beams; each detector assembly further comprising a detector subassembly and at least one circuit board assembly mechanically secured to the detector management system in thermal communication, with data acquisition chips to reduce the variation in temperature in the detector assembly, each thermal management system including a heat sink assembly comprising a substantially rigid thermally conductive spreader plate disposed over two or more integrated circuits to uniformly distribute the thermal energy generated by the integrated circuits during operation and at least one conductive heat pipe carrying a heat exchange fluid; the heat pipe being in thermal communication with the spreader plate.

* * * * *

UNITED STATES PATENT AND TRADEMARK OFFICE
CERTIFICATE OF CORRECTION

PATENT NO. : 6,931,092 B2  Page 1 of 1
APPLICATION NO. : 10/609755
DATED : August 16, 2005
INVENTOR(S) : Ashutosh Josh et al.

It is certified that error appears in the above-identified patent and that said Letters Patent is hereby corrected as shown below:

In column 6, line 54, "spreader plate 66" should be amended to read --spreader plate 76--.

In column 14, line 15, after the word "detector", add the following: --subassembly via a flexible connection, each circuit board assembly comprising a plurality of data acquistion chips attached to at least one printed circuit board and a thermal--.

Signed and Sealed this

Eighteenth Day of August, 2009

David J. Kappos
*Director of the United States Patent and Trademark Office*